(12) United States Patent
Flanders et al.

(10) Patent No.: US 8,467,051 B2
(45) Date of Patent: Jun. 18, 2013

(54) WIDELY-TUNABLE SEMICONDUCTOR SOURCE INTEGRATED IN WINDOWED HERMETIC PACKAGE

(75) Inventors: Dale C. Flanders, Lexington, MA (US); Petros Kotidis, Framingham, MA (US)

(73) Assignee: Axsun Technologies, Inc., Billerica, MA (US)

(*) Notice: Subject to any disclaimer, the term of this patent is extended or adjusted under 35 U.S.C. 154(b) by 0 days.

(21) Appl. No.: 13/421,012

(22) Filed: Mar. 15, 2012

(65) Prior Publication Data

US 2012/0199745 A1    Aug. 9, 2012

Related U.S. Application Data

(63) Continuation of application No. 12/115,335, filed on May 5, 2008, now Pat. No. 8,164,748, which is a continuation-in-part of application No. 11/948,520, filed on Nov. 30, 2007, now abandoned.

(60) Provisional application No. 60/867,849, filed on Nov. 30, 2006.

(51) Int. Cl.
    *G01J 3/00* (2006.01)
(52) U.S. Cl.
    USPC ............................................. 356/300
(58) Field of Classification Search
    USPC ............................................. 356/300
    See application file for complete search history.

(56) References Cited

U.S. PATENT DOCUMENTS

| 6,953,487 B2 | 10/2005 | Cliche et al. |
| 2005/0165315 A1 | 7/2005 | Zuluaga et al. |
| 2005/0248758 A1 | 11/2005 | Carron et al. |
| 2006/0215713 A1 | 9/2006 | Flanders et al. |

OTHER PUBLICATIONS

Frish, M.B. et al., "Standoff gas leak detectors based on tunable diode laser absorption spectroscopy," Proceedings of the SPIE, vol. 6010, 2005, pp. 60100D-1 to 60100D-9.

Johnstone, W. et al., "Tuneable diode laser spectroscopy over optical fibres for gas measurements in harsh industrial environments," Proceedings of the SPIE, vol. 5952, 2005: pp. 595206-1 to 595206-8.

*Primary Examiner* — Tarifur Chowdhury
*Assistant Examiner* — Abdullahi Nur
(74) *Attorney, Agent, or Firm* — Houston & Associates, LLP (57) ABSTRACT

A near infrared (NIR) semiconductor laser system is shown for gas sensing. An embodiment is centered on the use of a system with a much wider tunable laser, which today has a scan band of more than 150 nanometers (nm) to as much as 250 nm or more. In some cases the scan band is about 400 nm or more. This is achieved in the current embodiment through the use of a widely tunable microelectromechanical system (MEMS) based Fabry-Perot filter as an integral part of the laser cavity. Using this technology, these systems are capable of capturing a variety of gases in the any of the well-known spectroscopic scan bands, such as the OH, NH or CH. For example, a single laser with a 250 nm scan band window between 1550-1800 nm can capture ten or as many as twenty hydrocarbon-based gases simultaneously.

20 Claims, 6 Drawing Sheets

WIDELY-TUNABLE SEMICONDUCTOR SOURCE INTEGRATED IN WINDOWED HERMETIC PACKAGE

RELATED APPLICATIONS

This application is a Continuation of application Ser. No. 12/115,335, filed on May 5, 2008, which is a Continuation-in-Part of U.S. application Ser. No. 11/948,520, filed on Nov. 30, 2007, which claims the benefit under 35 USC 119(e) of U.S. Provisional Application No. 60/867,849, filed on Nov. 30, 2006, all of which are incorporated herein by reference in their entirety.

BACKGROUND OF THE INVENTION

Combustible gas detectors can be divided into two general categories. The first category includes a variety of "passive" technologies of which the electrocatalytic (catalytic bead) type is the most common. The second category is based on technology that uses infrared absorption as the detection modality.

Infrared (IR) absorption is considered "active" since an IR source emits a signal, usually many times a second, and the amount of energy falling on the detector serves as an active measure of the gas concentration at that moment. Any failure of the source or detector, or blockage of the signal by dirt, is detected immediately as a malfunction. For this reason, IR detectors are also considered to be fail-to-safe. IR gas detectors can be used for "point" (single location) or "open path" (line of sight) applications.

Electrocatalytic or "catalytic" detectors have been used for over 30 years and are widely deployed in a variety of industries as single-point detectors for combustible gases. They function on the relatively simple and reliable principle that a combustible gas can be oxidized to produce heat. The resulting temperature change can be converted, via a standard Wheatstone bridge, to a sensor signal. That signal can then be used to activate alarms and initiate fire preventative action. Even though these detectors can be manufactured to be very low cost, their primary drawback is that they can be contaminated or "poisoned" and they hence require dedicated user attention.

An alternative method of measuring gas concentration is based on absorption of infrared (IR) radiation at certain wavelengths as the optical signal passes through a volume of gas. Devices using this technology have a light source and a light detector and measure the light intensity at two specific wavelengths, one at an absorption (active) wavelength and one outside of the absorption (reference) wavelength. If a volume of gas passes between the source and detector, the amount of light in the active wavelength falling on the detector is reduced, while the amount of light in the reference wavelength remains unchanged. Much like the catalytic detectors, the gas concentration is determined from the relative difference between the two signals.

Generally, there are several key advantages to using IR-based detectors: immunity from chemical poisons; does not need oxygen or air to detect gas; can work in continuous exposure gas environments; fail-to-safe technology; and internal compensation can eliminate span drift.

SUMMARY OF THE INVENTION

Embodiments of the present invention concern the use of Near Infrared (NIR) semiconductor lasers for gas sensing. This technology is expected to address some of the limitations of the current IR detectors. Such limitations include the following: 1) interference from other gases or moisture, due to the mid-IR operation as well as the fact that these IR detectors are typically low resolution and cover a limited spectral range, which prevents them from being able to identify and correct for the interfering gases; 2) inability to detect multiple gases with a single device, since these detectors use fairly coarse optical filters over a specific spectral range and therefore cannot detect gases with spectral signatures outside that window; and 3) limited sensitivity due to low signal-to-noise ratio, which is primarily attributed to the use of mid-IR sensitive detectors (pyroelectric), which are typically not as sensitive as InGaAs detectors.

The key elements of embodiments of the invention often include a number of aspects.

The use of a widely-tuned semiconductor laser is important. Currently there are laser-based gas detectors that use a technology called Tunable Diode Laser Absorption Spectroscopy (TDLAS), but these devices are very narrow in spectral range (10-60 nanometers (nm)) and they use a dithering technique to monitor individual gases. It is not possible to use these devices to monitor multiple gases. An embodiment of the invention is centered on the use of a system with a much wider tunable laser, which today has a scan band of more than 150 nm to as much as 250 nm or more. In some cases the scan band is about 400 nm or more. This is achieved in the current embodiment through the use of a widely tunable microelectro-mechanical system (MEMS) based Fabry-Perot filter as an integral part of the laser cavity. Using this technology, these systems are capable of capturing a variety of gases in the any of the well-known spectroscopic scan bands, such as the OH, NH or CH. For example, a single laser with a 250 nm scan band window between 1550-1800 nm can capture ten or as many as twenty hydrocarbon-based gases simultaneously.

High resolution spectroscopy is provided by use of the MEMS Fabry-Perot filter, which enables the potential for operation at very high resolution (as high as $0.1$ cm$^{-1}$), which allows the system to identify fine spectral features of the interfering gases (such as moisture) and correct for them, providing a much more accurate reading.

High sensitivity measurements are further enabled, providing applicability beyond the detection of explosive or flammable gases, to be used for any gas, liquid or solid spectral measurement, assuming that the gas, liquid or solid in question absorbs infrared radiation.

The preferred embodiment also provides for on-board referencing. Also the higher SNR of embodiments leads to higher measurement speed and hence there is a tradeoff option between laser power, detector sensitivity and measurement speed depending on the application requirements. Further small explosion proof packaging is preferably provided. The use of miniaturized packages allows for reduced requirements on the size of the explosion proof housing. Also, the highly efficient NIR semiconductor lasers allow for minimal power consumption and potentially improving battery life, if used. In the preferred embodiment, the system includes wireless communication.

In general, according to one aspect, the invention features a spectroscopy system. The system comprises a hermetic package with at least one optical port for coupling an optical beam from the hermetic package to a sample and back into the hermetic package. An optical bench is installed within the hermetic package, and a tunable laser is installed on the optical bench for generating the optical beam. A signal detector is further provided on the bench for detecting the optical beam received in through the optical port from the sample.

Also, a controller spectrally analyzes the sample from a response of the signal detector.

In embodiments, a housing contains the hermetic package, the housing comprises a sample port for receiving the sample and the optical beam from the hermetic package into the sample port. A mirror is preferably installed in the sample port for reflecting the optical beam back into the optical port.

Additional possible features include a battery for powering the controller and the tunable laser and a wireless interface for providing wireless communication of spectral analysis information from the controller.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
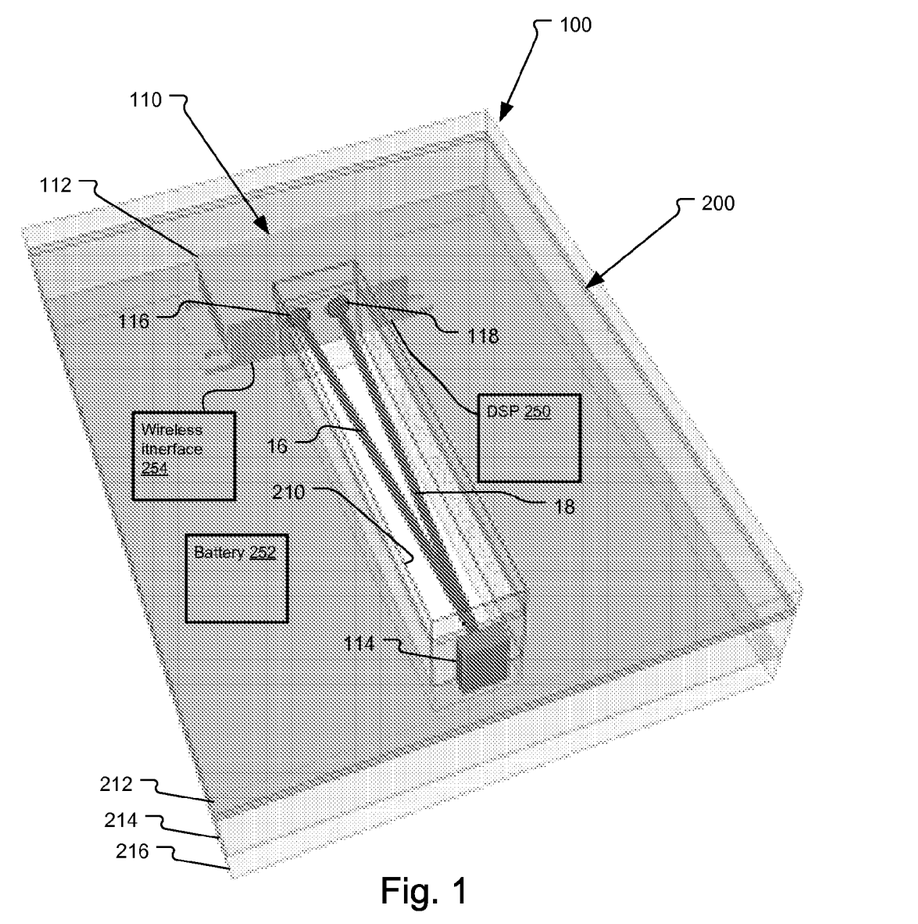
FIG. 1 is a perspective view of a system for gas detection and analysis according to an embodiment of the present invention.

FIG. 1 shows a system 100 for gas detection and analysis, which has been constructed according to the principles of the present invention.

Generally, detection of several gases that have spectroscopic signatures in the near-infrared zone of 1.3-2 micrometers are detected by using a single-chip tunable source covering 200-300 nanometer (nm) scan band in this zone. Such gases include most of the common hydrocarbons, such as methane, ethane, ethylene, acetylene and other types, such as ammonia. The detection limits for the system are preferably in the 10% of lower explosion limit (LEL) levels.

The gas sensor system 100 preferably comprises three basic functional components: an optical module 110, an electronics board 250, and a gas sample optical interface.

The optical module 110 comprises a single hermetically sealed butterfly package 112, which contains all of the active optical functions of the system 100 assembled on a single micro-optical bench 105: a widely tunable semiconductor laser, optical amplitude and wavelength reference detectors, and the signal detector.

The optical module 110 produces a collimated optical beam output 16 into the gas sample optical interface. Specifically, this beam 16 interacts with the sample gas in an optical sample interface port 210 in a housing 200, using one or more bounces in an external mirror arrangement in order to accumulate a sufficient optical absorption path length.

The returning beam 18 from the gas sample optical interface is detected by the signal detector inside the optical module 110.

The beam exits and enters the hermetic package 112 via at least one optical port 116, 118, comprising at least one window being transparent to the optical beam. This window is formed as part of an outer wall of the hermetic package 112.

The electronics board 250 contains analog and digital components for controlling tunable laser scanning, detecting and digitally processing the return signal, and outputting the gas sensing data in the digital format. In some examples, external system control and data upload are provided via a wireless interface 254. Also, in examples, the system 100 includes a battery 252 for main system power and/or backup power.

In more detail, the system housing 200 comprises a base plate 216. A frame unit 214 is installed and sealed to this base plate 216. Generally, the frame unit 214 of the housing 200 provides a hollow internal area in which the optical module 110 and specifically the butterfly package 112 is installed. The hollow internal area further houses the wireless interface 254, the battery 252 and the digital signal processing electronics board 250. A top cap 212 is sealed to the frame member 214 to seal the internal area and thus the electronic and optical components.

An optical sample interface port 210 is formed in the housing 200 and specifically the frame member 214, base plate 216 and the top member 212. The optical sample interface port 210 mechanically interfaces with the output optical port 216 and the input optical port 218, which are formed on the side wall of the butterfly package 112. At the far lateral end of the optical sample interface port 210, a mirror 114 is provided to couple the output beam 116 as the input beam 118 between the output optical port 116 and the input optical port 118.

In the preferred embodiment, the output optical port 116 and the input optical port 118 comprise optically transparent windows. In some examples, these windows are bandpass filters that are limited to the scan band of the system 100 to thereby to prevent interference from external light sources.

While the applicability of the system is described in the context of gas analysis, the system 100 also has application in fluid and solid analysis. In some of these applications, the system uses the mirror 114 where the gas, liquid or solid sample is transmissive. When it is opaque to the wavelengths within the scan band, the system collects the diffusely reflected light from the sample for analysis.

Figure 2:
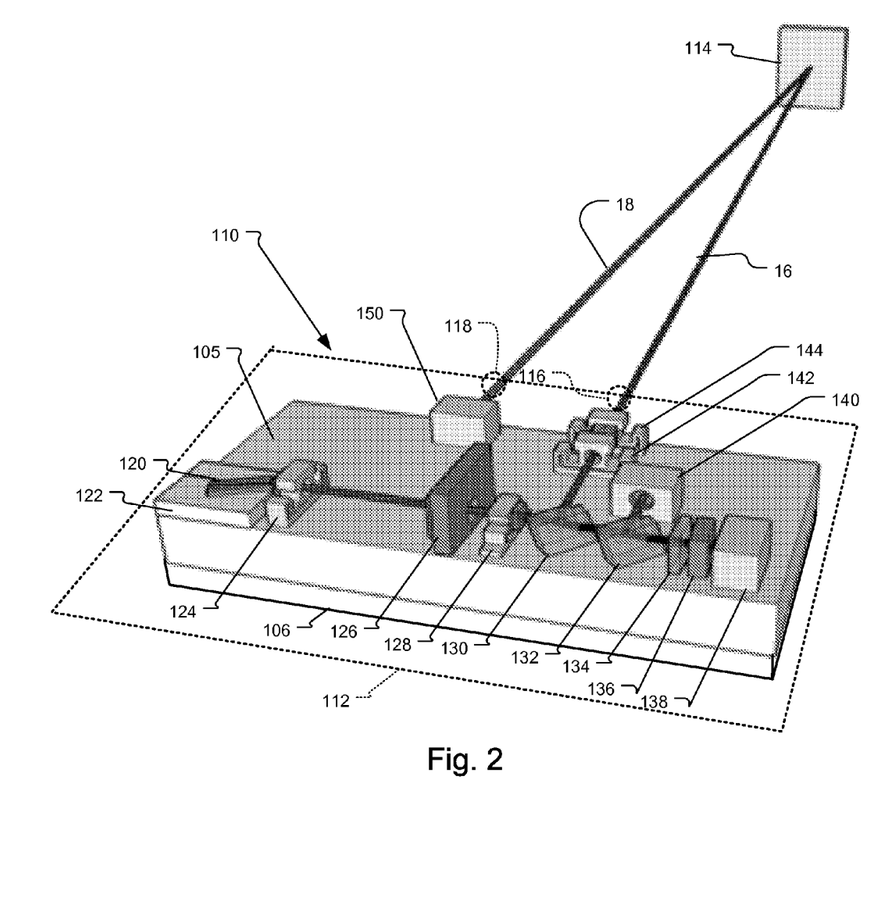
FIG. 2 is a perspective view of the system for gas detection and analysis showing the optical bench layout according to an embodiment of the present invention.

FIG. 2 illustrates the internal optical components 111 of the gas sensor optical module 110 within the hermetic package 112 including the micro-optical bench layout.

The widely tunable external cavity semiconductor laser comprises a semiconductor gain chip 120 which is installed on the optical bench 105 via a submount substrate 122. A micro-electro-mechanical (MEMS) tunable optical filter 126 provides narrowband tunable feedback into the gain chip 120. An intervening intracavity lens component 124 couples light between the chip 120 and the MEMS filter 126.

In a current embodiment, the laser is as described in US 20060215713 A1, entitled Laser with Tilted Multi Spatial Mode Resonator Tuning Element, by Flanders, et al. This application is incorporated herein in its entirety by this reference.

A sample of the output beam 16 is provided from a collimating lens 128 to two taps 130, 132 to an amplitude detector 140 and a wavelength reference detector 138. For wavelength referencing, a fixed wavelength etalon 134 and a possible a cut-off filter 136 are placed in front of the wavelength detector 138 to provide wavelength calibration reference for the wavelength scanning output laser signal, along with the amplitude information provided by the amplitude detector 140.

A combination of two series output lens 142 and 144 are used for both collimating the output beam 16, received from the collimating lens component 128 and the first tap 130, at the proper beam diameter and for finely steering the beam 16 for alignment to the optical gas sampling interface outside the optical package 112. Specifically, the beam is steered to be coupled back into the package 112 via input port 118 and detected by signal detector 150.

The return optical signal detector 150 is integrated on the same micro-optical bench 105.

In the preferred embodiment, the optical bench 105 is temperature controlled. This is provided by a thermoelectric cooler 106.

The requirements for explosive gas monitoring are: that the systems are capable of detecting down to 10% of the Lower Explosive Limit (LEL) for each gas. For methane, this limit is 5%, so the detectors must be accurate to 0.5%. However, regulatory and safety requirements are pushing these limits down, and there is a need for higher sensitivity devices. Operation at the near infrared (NIR) regime for the present system 100 allows for the use of more sensitive detectors, such as InGaAs rather than pyroelectric, as it is currently the case with existing IR sensors. In addition, the use of semiconductor, high power lasers allows for higher signal-to-noise ratio measurements, which directly translates to lower sensitivity limits.

Figure 3:
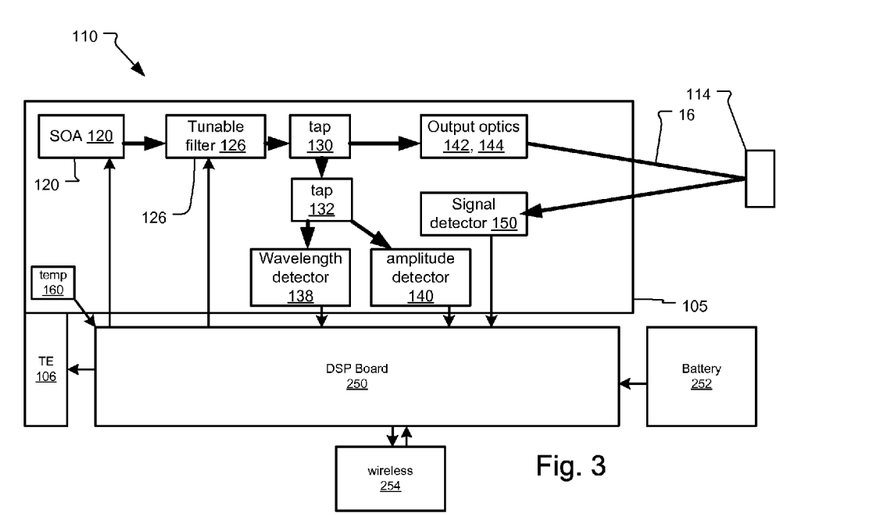
FIG. 3 is a block diagram view of the system for gas detection and analysis showing relationship between the optical bench layout and system electronics according to an embodiment of the present invention.

FIG. 3 illustrates the relationship between the electronics and the optical bench 105 in a current embodiment of the invention. Specifically, a digital signal processing board 250 controls power to the gain chip 120 and the tuning of the tunable filter 126. Digital signal board 250 receives the response of the signal detector 150.

By analyzing the response of the signal detector in conjunction with the information from the wavelength detector 138 and the amplitude detector 140, the digital signal processor 250 resolves the spectral response of the gas sample within the gas port. Further, the digital signal processor 250 monitors the temperature of the optical bench 105 via a temperature detector 160, such as a thermistor, which is typically installed on the surface of the bench 105. Using this feedback, the digital signal processor board 250 drives the thermoelectric cooler 106 to temperature stabilize the optical bench 105.

In one embodiment, the system is also provided with a battery 252 for power. Further, a wireless interface 254 is used in some examples to both provide control to the spectral analysis system 110 and also provide data upload to a host system.

Figure 4:
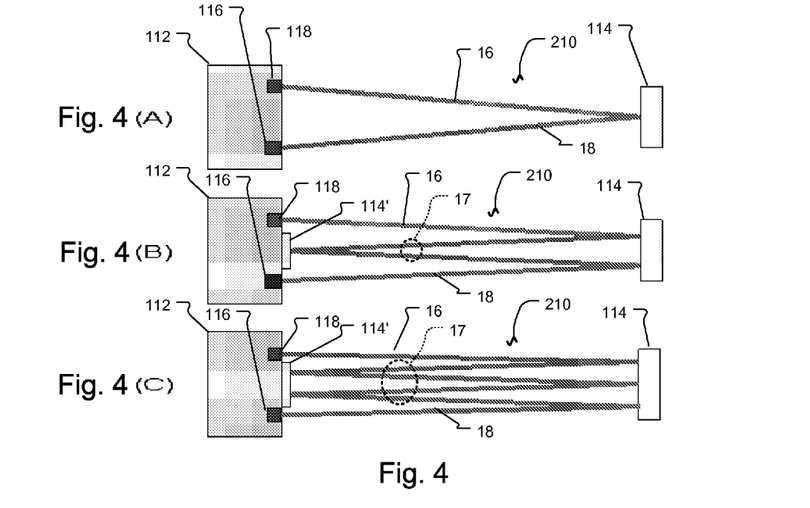
FIGS. 4A, 4B, and 4C show three variations for optical interface to the gas sample port, single bounce, double bounce and triple bounce, according to embodiments of the present invention.

FIGS. 4A through 4C illustrate a number of examples for configuring the beams in the gas interface port 210. FIG. 4A shows one example where the output beam 16 is reflected to form the input beam 18 by the mirror 114 in a single bounce arrangement.

In FIG. 4B, a double bounce arrangement is used in which a second mirror 114' is added optically between the output port 118 and the input port 116 of the hermetic package 112. Specifically, this doubles the beam path length by yielding passes 117 through port 210.

FIG. 4C illustrates a triple bounce arrangement in which the output beam 16 is reflected between mirrors 114 and 114' three times before returning to the input port 118.

Figure 5:
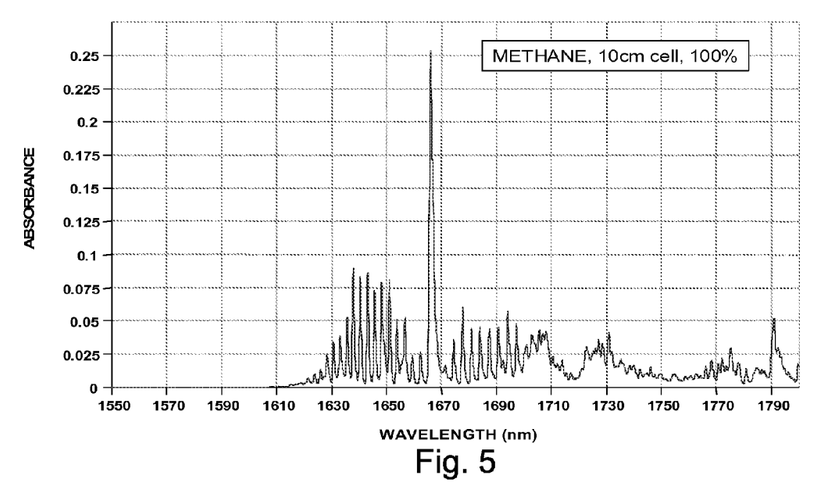
FIG. 5 is a plot of absorbance as a function of wavelength in nanometers for 100% methane measured by the system.
Figure 6:
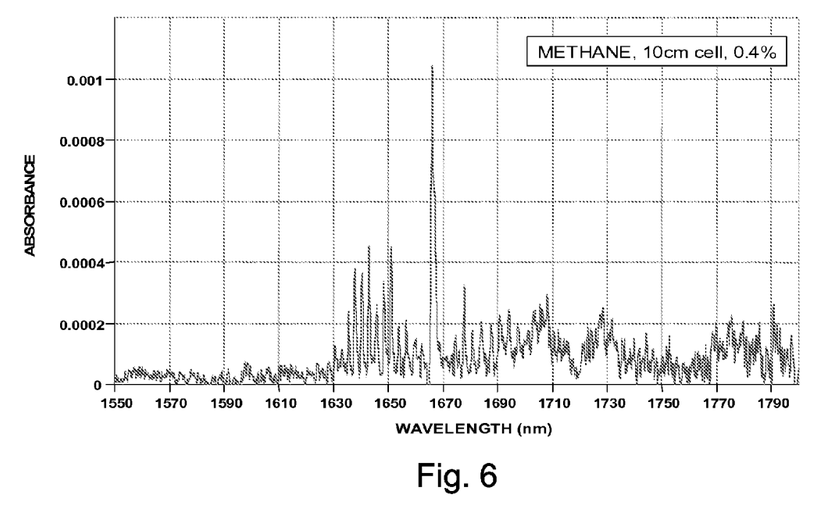
FIG. 6 is a plot of absorbance as a function of wavelength in nanometers for 0.4% methane measured by the system.

FIGS. 5 and 6 are plots of absorbance as function of wavelength in nanometers for methane gas sensing spectra at 100% and 0.4% concentration levels using a single pass 10 centimeter (cm) absorption cell, which were obtained using the system 100 for gas detection and analysis. The methane Lower Explosive Limit (LEL) is 5.0% and the required sensing level of 10% LEL is 0.5%. High signal to noise ratios of the spectra shows that methane can be sensed to very low concentrations.

Figure 7:
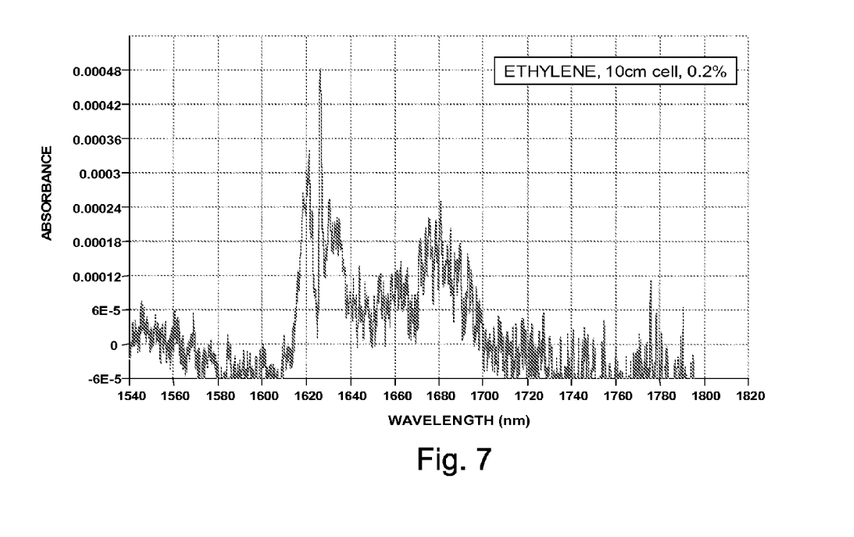
FIG. 7 is a plot of absorbance as a function of wavelength in nanometers for 0.2% ethylene measured by the system.

FIG. 7 shows a similar gas-sensing spectrum for ethylene gas in a 10 cm path cell, illustrating simple sensing of different gases using the spectroscopic gas system. Such system also potentially allows measurement of mixtures of multiple gases.

Figure 8:
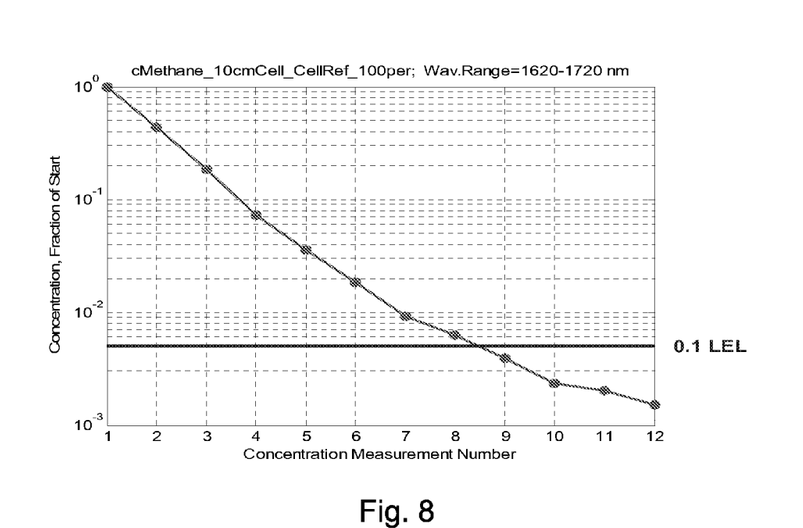
FIG. 8 is a plot of concentration as a function of time in measurement cycle for a methane sample measured by the system.

FIG. 8 illustrates concentration measurements of methane gas in a 10 cm path cell using gas sensor 100, where gas concentration number is extracted from the measured spectra. Methane gas concentration is measured down to the 0.15% level, which is equivalent to the 0.03*LEL level. Gas detection sensitivity can be enhanced even further by using a very compact multi-pass gas cell allowed by the single transverse mode optical beam of the sensor.

Figure 9:
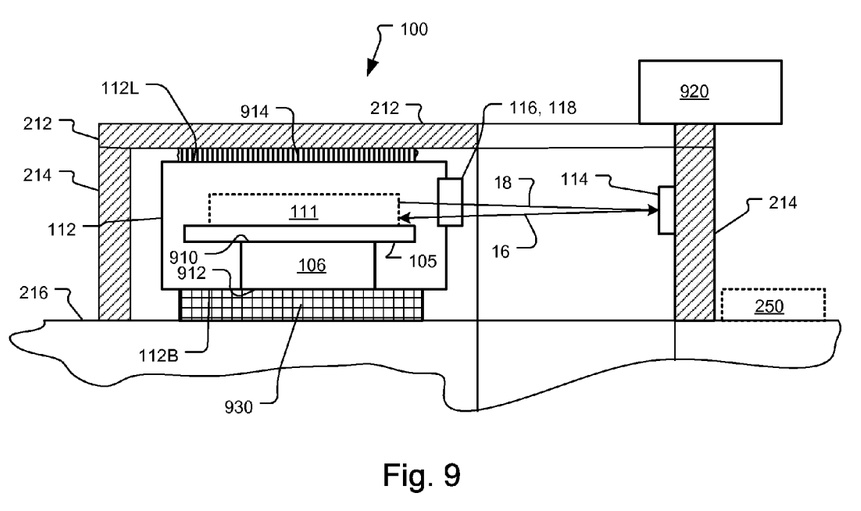
FIG. 9 illustrates is a schematic cross-sectional view of the gas sensor system illustrating the thermal dissipation scheme according to the present invention.

FIG. 9 illustrates the thermal dissipation paths of the gas sensor system 100 that prevent the optical ports 116, 118 and mirror 114 from accumulating condensation.

In the preferred embodiment, the optical ports 116, 118 and/or mirror 114 are held at temperatures above ambient temperature. As a result, even in highly saturated environments, condensation will be prevented from forming on the optical ports 116, 118 and/or mirror 114.

Elevated temperatures for the optical ports 116, 118 and/or mirror 114 are achieved in one embodiment by including heaters near or on the optical ports 116, 118 and/or the mirror 114. Simple resistive heaters are used in some examples.

However, in the preferred embodiments, the thermal dissipation paths for the optical system 111 and/or electronic system 250 are judiciously designed to provide these elevated temperatures.

In one example, the thermal dissipation path for heat generated by the thermoelectric cooler 106 is designed to extend through to the lid 112L of the hermetic package 112. In more detail, the thermoelectric cooler 106 has a hot side 912 and cool side 910. The hot side 912 is thermally coupled to the bottom 112B of the hermetic package 112 as is conventional. However, a thermally insulating layer or air or vacuum 930 separates the bottom 112B of the package 112 from a thermal sink such as the baseplate 216. Instead, the thermal dissipation path is through the package 112 to the lid 112L. In one example, a thermally conductive paste is used to create a thermal path from the lid 112L to the cap 212. This thermal dissipation path through the package 112 and thus the ports 116, 118 of the package 112 ensures a heated state of the ports 116, 118 during operation of the system 100.

In a similar way, the mirror 114 is also included in a thermal dissipation path. In more detail, in one example, heat generated by the electronics of the DSP board 250 is dissipated through the portion of the frame member 214 that supports the mirror 114 to a thermal sink 920. As a result, the mirror 114 is passively heated by the "waste" heat generated by the electronics 250 to ensure that the mirror 114 is hotter than the environment during operation, thereby preventing the accumulation of condensation on the mirror 114.

While this invention has been particularly shown and described with references to preferred embodiments thereof, it will be understood by those skilled in the art that various changes in form and details may be made therein without departing from the scope of the invention.

What is claimed is:

1. An integrated optical analysis system, the system comprising: a hermetic package with at least one optical port through which an optical beam is coupled from an inside of the hermetic package to a sample, wherein the at least one optical port comprises a window that is transparent to the tunable optical signal and functions as part of an outer wall of the hermetic package; a port heat source for heating the at least one optical port; an optical bench within the hermetic package; a tunable source on the optical bench for generating the optical beam that is scanned in wavelength over a scan band; a signal detector on the bench and in the hermetic package for detecting the optical beam received in through the at least one optical port from the sample; and a battery for powering a controller and the tunable source.

2. The system as claimed in claim 1, wherein the port heat source is a thermoelectric cooler for controlling a temperature of an optical system in the hermetic package.

3. The system as claimed in claim 1, further comprising a mirror for coupling the optical beam between the at least one optical port and a sample and back to the hermetic package.

4. The system as claimed in claim 3, wherein the sample is located outside of the hermetic package.

5. The system as claimed in claim 3, further comprising a mirror heat source for heating the mirror.

6. The system as claimed in claim 5, wherein the mirror heat source is electronics for operating the integrated optical analysis system.

7. The system as claimed in claim 6, wherein the mirror heat source heats the mirror to a temperature greater than the surrounding environment to prevent condensation on the mirror during operation.

8. The system as claimed in claim 1, further comprising a thermally insulating layer that separates the hermetic package from a thermal sink.

9. The system as claimed in claim 1, wherein the port heat source heats the at least one optical port during operation of the integrated optical analysis system.

10. The system as claimed in claim 1, further comprising a thermal dissipation path through the hermetic package to a lid of the hermetic package.

11. The system as claimed in claim 1, further comprising a wavelength detector to provide wavelength calibration reference for a wavelength scanning output laser signal.

12. The system as claimed in claim 1, wherein the window is a bandpass filter that is limited to the scan band of the system.

13. The system as claimed in claim 1, wherein the tunable source is a single-chip tunable laser having a scan band of 200-300 nanometers.

14. The system as claimed in claim 1, wherein the tunable source comprises a gain chip and a Fabry-Perot tunable filter for filtering an emission from the gain chip.

15. The system as claimed in claim 1, wherein the tunable source is a tunable laser having a scan band of 150 nanometers to 250 nanometers.

16. The system as claimed in claim 1, wherein the tunable source is a tunable laser having a scan band greater than 400 nanometers.

17. The system as claimed in claim 1, further comprising a wireless interface that provides wireless communication of analysis information from the controller to a host system.

18. The system as claimed in claim 1, wherein the port heat source is energized when the tunable source is generating the optical beam.

19. The system as claimed in claim 1, wherein the port heat source is a resistive heater.

20. An integrated optical analysis system, the system comprising: a hermetic package with at least one optical port through which an optical beam is coupled from an inside of the hermetic package; and an optical bench within the hermetic package; a tunable source on the optical bench for generating the optical beam that is scanned in wavelength over a scan band; a signal detector on the bench and in the hermetic package for detecting the optical beam received in through the at least one optical port from the sample; a controller that monitors the response of the signal detector and generates analysis information; a battery for powering the controller and the tunable source; and a wireless interface that provides wireless communication of the analysis information from the controller to a host system.

* * * * *